(12) United States Patent
Modawar

(10) Patent No.: US 9,448,156 B2
(45) Date of Patent: Sep. 20, 2016

(54) OPTICAL PARTICLE ANALYSIS

(71) Applicant: Moxtek, Inc., Orem, UT (US)

(72) Inventor: Faris Modawar, Orem, UT (US)

(73) Assignee: Moxtek, Inc., Orem, UT (US)

( * ) Notice: Subject to any disclaimer, the term of this patent is extended or adjusted under 35 U.S.C. 154(b) by 60 days.

(21) Appl. No.: 14/606,848

(22) Filed: Jan. 27, 2015

(65) Prior Publication Data

US 2015/0268151 A1 Sep. 24, 2015

Related U.S. Application Data

(60) Provisional application No. 61/955,573, filed on Mar. 19, 2014.

(51) Int. Cl.
*G01N 21/21* (2006.01)
*G01N 15/14* (2006.01)
*G01N 21/53* (2006.01)
*G01N 21/05* (2006.01)

(52) U.S. Cl.
CPC ...... *G01N 15/1436* (2013.01); *G01N 15/1468* (2013.01); *G01N 21/05* (2013.01); *G01N 21/21* (2013.01); *G01N 21/53* (2013.01); G01N 2015/1454 (2013.01); G01N 2015/1493 (2013.01); G01N 2015/1497 (2013.01); G01N 2021/216 (2013.01)

(58) Field of Classification Search
CPC ...... G01N 21/00; G01N 21/21; G01N 21/53; G01N 15/1436
USPC .................................................. 356/491, 494
See application file for complete search history.

(56) References Cited

U.S. PATENT DOCUMENTS

| | | | |
|---|---|---|---|
| 5,104,221 A | 4/1992 | Bott et al. | |
| 6,859,276 B2* | 2/2005 | Xu | G01N 15/0211 356/336 |
| 7,030,981 B2* | 4/2006 | Bishop | G01N 21/211 356/365 |
| 7,660,036 B2 | 2/2010 | Metzger | |
| 7,936,457 B2 | 5/2011 | Yang | |
| 8,345,239 B1 | 1/2013 | Sieracki et al. | |
| 2012/0044493 A1 | 2/2012 | Smart et al. | |
| 2013/0004987 A1 | 1/2013 | Lo et al. | |

OTHER PUBLICATIONS

PCT Application No. PCT/US2015/013323: Filing date Jan. 28, 2015; Moxtek Inc. et al.; International Search Report mailed May 4, 2015.

* cited by examiner

*Primary Examiner* — Jonathan Hansen
(74) *Attorney, Agent, or Firm* — Thorpe, North & Western, LLP

(57) ABSTRACT

A system and method for determining particle size, shape, and/or quantity. The particle can alter the polarization state of two oppositely-polarized light beams, thus allowing the light beams to interfere with each other. An interference pattern from interference of the two light beams can be captured by a CCD. The interference pattern can be analyzed to determine size, shape, and/or quantity.

25 Claims, 3 Drawing Sheets

OPTICAL PARTICLE ANALYSIS

PRIORITY CLAIM(S)

Priority is claimed to copending U.S. Provisional Patent Application No. 61/955,573, filed Mar. 19, 2014, which is hereby incorporated herein by reference.

FIELD OF THE INVENTION

The present application is related generally to determination of microscopic particle size, shape, and quantity.

BACKGROUND

Particulate contamination can be problematic in many industries. For example, large particulate contamination in a liquid medicine can clog the needle. A clean room for a manufacturing process (e.g. semiconductor manufacturing) may require very pure air because particles can cause defects in the manufactured product. Abrasive particles in lubricating oil can cause rapid wear of moving parts.

Detection and analysis of the contamination can be a first step in resolving the contamination problem. It can be helpful to know the quantity of particulates. For example, knowledge that the particle count in a clean room has recently increased can alert engineers to find and stop the source. It can be helpful to know particle size and shape because such knowledge may help the manufacturing engineer to determine the source of the contamination. Also, if the contaminant is in lubricating oil, knowledge of particle size and shape can help the engineer determine the severity of the problem (some particle sizes and/or shapes) may cause more rapid erosion than other particles).

In other situations, the particles may be desirable, but it can be important to know the quantity, size, and/or shape of the particles.

Information relevant to attempts to address these problems can be found in U.S. Pat. No. 8,345,239 and U.S. Patent Publication Number 2013/0004987.

SUMMARY

It has been recognized that it would be advantageous to determine particle size, shape, and/or quantity. The present invention is directed to particle analysis systems and to methods of determining particle size, shape, and/or quantity that satisfy these needs. Each embodiment may satisfy one, some, or all of these needs.

The particle analysis system can comprise two polarized light emitters, oppositely-polarized with respect to each other, disposed at a perimeter of a fluid-flow region, and capable of emitting two beams of oppositely polarized light through the fluid-flow region and onto a charge couple device camera (CCD).

The method of determining particle size, shape, and/or quantity can comprise the following:
1. Emitting two polarized light beams, that are oppositely polarized with respect to each other, into a fluid flow region.
2. Passing a particle in the fluid flow region past the two light beams with the particle changing the polarization states of the light beams so that the light beams interfere with each other, after passing the particle, to form an interference pattern.
3. Exposing a charge couple device camera (CCD) to the interference pattern.

BRIEF DESCRIPTION OF THE DRAWINGS

FIGS. 1 & 2 also illustrate methods of determining particle size, shape, and/or quantity, in accordance with embodiments of the present invention.

DEFINITION

Figure 1:
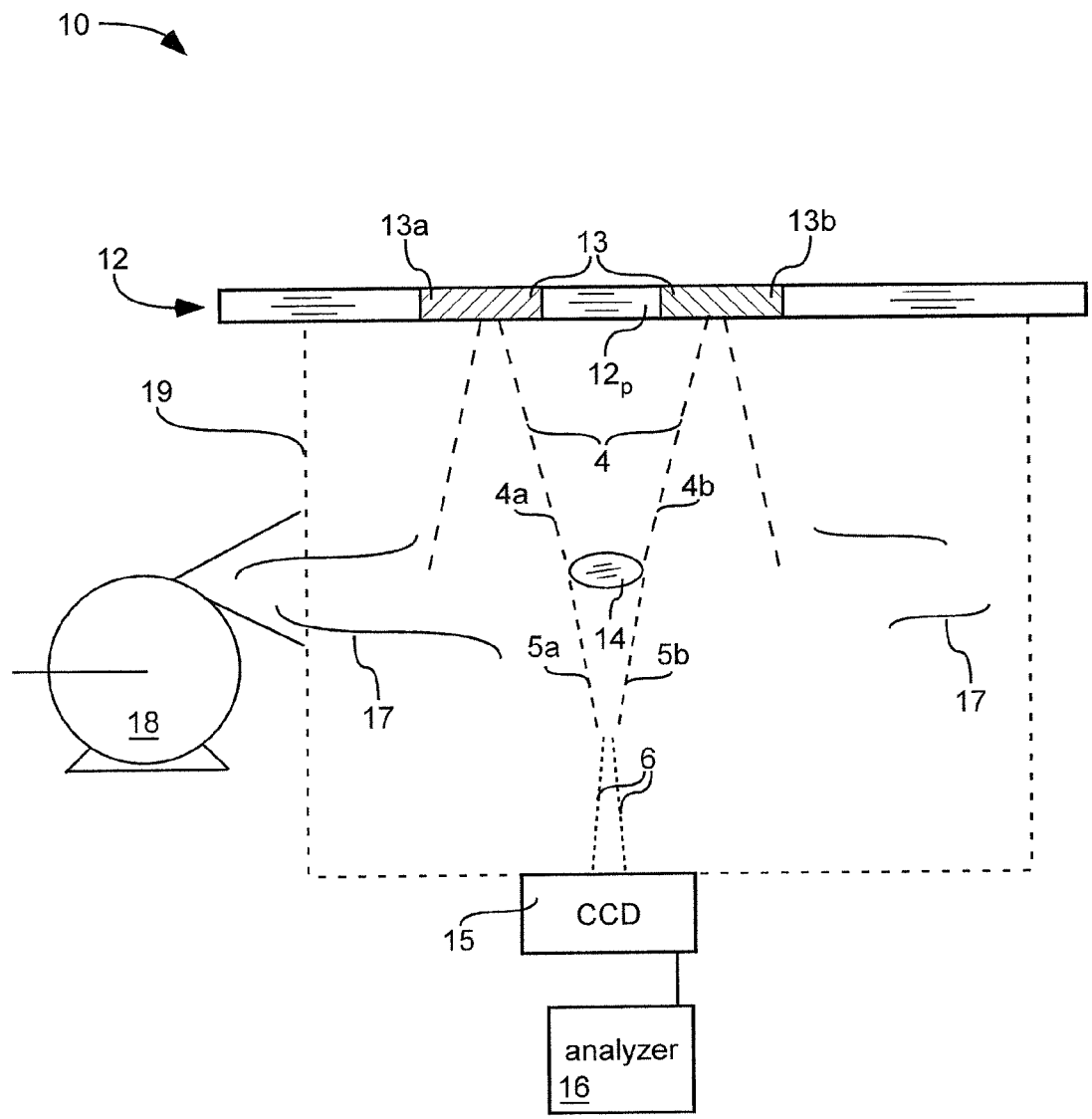
FIGS. 1 & 2 are schematic cross-sectional side views of particle analysis systems 10 and 20, in accordance with embodiments of the present invention.

As used herein, the term "oppositely-polarized" means that one light beam (e.g. 4a) has one polarization (e.g. s or clockwise polarization) and the other light beam (e.g. 4b) has an opposite polarization (e.g. p or counterclockwise polarization, respectively). Following are examples of how to create oppositely-polarized light beams 4a and 4b as defined herein:
1. The two polarization devices 23 are two linear polarizers 23a and 23b and the linear polarizers 23 are rotated perpendicularly with respect to each other (i.e. wires or other polarizing elements of the two linear polarizers 23a and 23b are disposed at a 90° angle with respect to each other).
2. The two polarization devices 23 are two circular-polarizers 23a and 23b. If each circular-polarizer 23 includes a linear polarizer and a quarter-wave plate, then emitted light beams 4a and 4b will be oppositely and circularly polarized if:
   a. The fast axis of each quarter-wave plate is rotated 45° with respect to wires of its associated linear polarizer.
   b. The two linear polarizers or the two quarter-wave plates are rotated 90° with respect to each other.
3. The light emitters 13 are two lasers and are rotated at a 90° angle with respect to each other, thus emitting an s-polarized light beam and a p-polarized light beam.

As used herein, the term "polarization device" means a linear polarizer or a circular-polarizer.

DETAILED DESCRIPTION

As illustrated in FIG. 1, a particle analysis system 10 is shown comprising two polarized light emitters 13, oppositely-polarized with respect to each other, disposed at a perimeter of a fluid-flow region 19, and capable of emitting two beams of oppositely polarized light through the fluid-flow region 19 and onto a charge couple device camera (CCD) 15. The two light emitters 13 can be any device that emits polarized light 4, such as for example a laser or a light source and a polarizer. The light emitters 13 can be disposed in a light-blocking screen 12. The light blocking screen can be opaque and can have two openings therein to receive the two polarization devices or light emitters, respectively. The light-blocking screen 12 can form at least part of a perimeter of the fluid-flow region 19.

Figure 2:
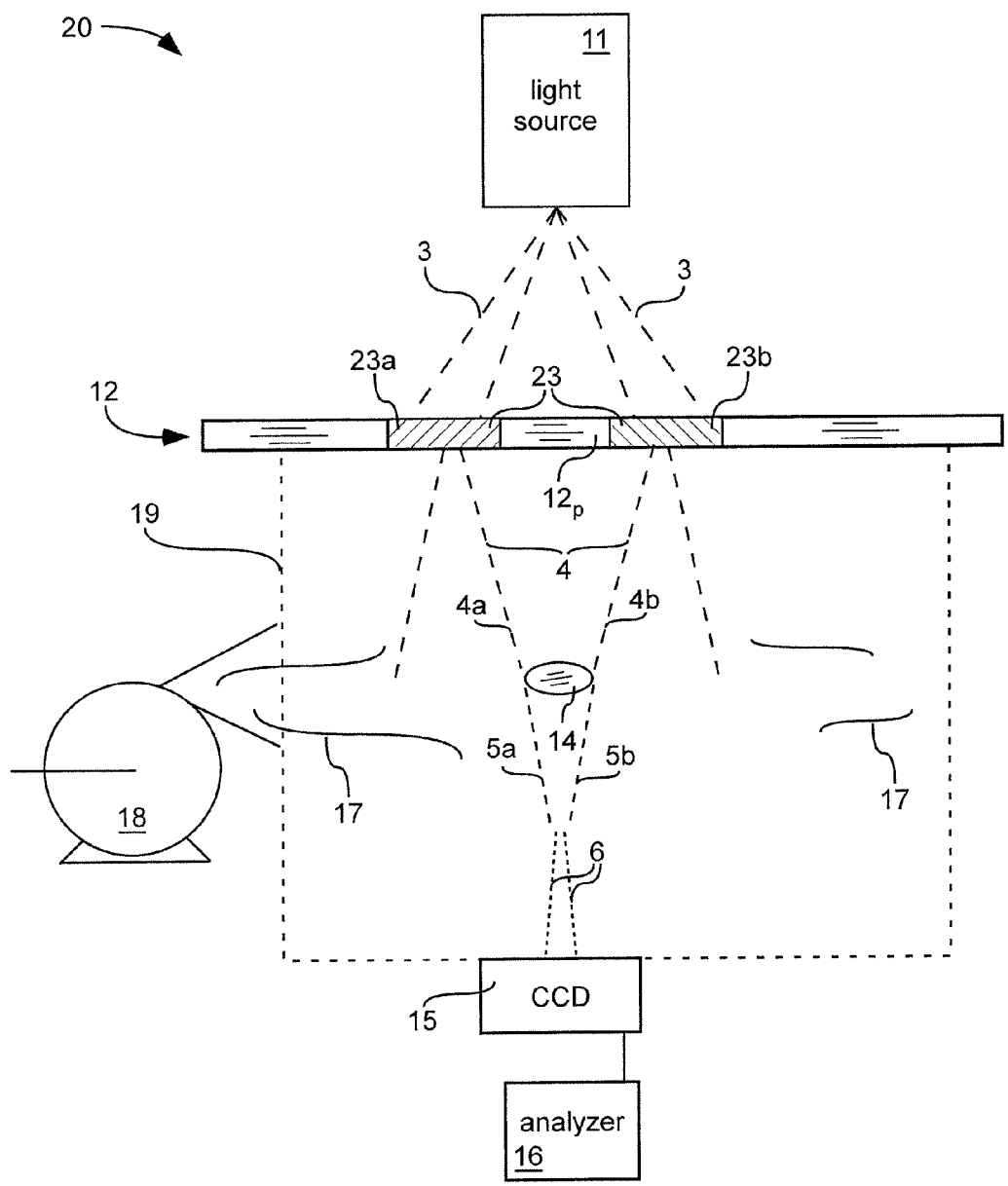

As shown in FIG. 2, the particle analysis system 20 can further include an unpolarized light source 11 directed towards the CCD 15. The fluid-flow region 19 can be disposed between the light source 11 and the CCD 15. A light-blocking screen 12 can be disposed between the light source 11 and the fluid-flow region 19. Two polarization devices 23, oppositely-polarized with respect to each other, can be disposed in the screen 12. The particle analysis system 20 can allow light 3 from the light source 11 to pass through each polarization device 23, through the fluid-flow region 19, and onto the CCD 15. Thus, the two polarized light emitters 13 shown in FIG. 1 can include a light source 11 combined with two polarization devices 23, as shown in FIG. 2.

Figure 3:
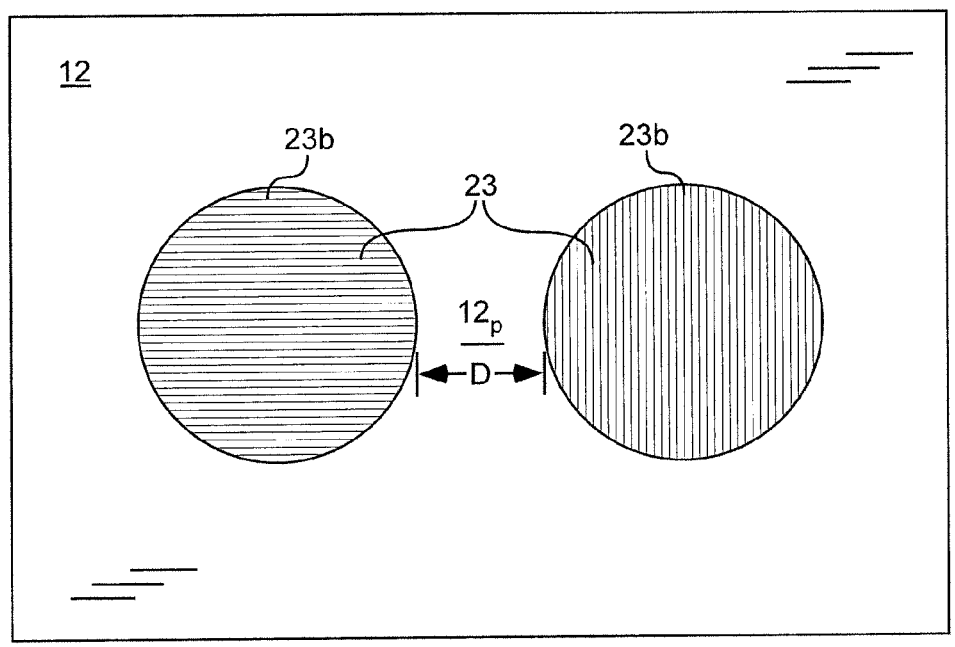
FIG. 3 is a schematic front view of two oppositely-polarized linear polarizers in a light-blocking screen, in accordance with embodiments of the present invention

As shown on the particle analysis system 30 in FIG. 3, the two polarization devices 23 can be two linear polarizers 23a and 23b. The linear polarizers 23a and 23b can be rotated perpendicularly with respect to each other (i.e. wires or other polarizing elements of the two linear polarizers can be disposed at a 90° angle with respect to each other).

As shown in FIG. 2, the light source can emit unpolarized light 3 towards the linear polarizers 23; then dual, oppositely-polarized light beams 4a and 4b can emit, from polarizers 23a and 23b respectively, into the fluid-flow region 19. One linear polarizer (e.g. 23a) can transmit p-polarized light (e.g. 4a) and reflect or absorb s-polarized light and the other linear polarizer (e.g. 23b) can transmit s-polarized light (e.g. 4b) and reflect or absorb p-polarized light.

The two polarization devices 23 can be two circular-polarizers 23, oppositely-polarized with respect to each other. One circular-polarizer (e.g. 23a) can emit clockwise polarized light (e.g. 4a) and the other circular-polarizer (e.g. 23b) can emit counterclockwise polarized light (e.g. 4b). Each circular-polarizer 23 can include a linear polarizer and a quarter-wave plate. Each linear polarizer can be disposed closer to the light source 11 than the quarter-wave plate. The fast axis of each quarter-wave plate can be rotated 45° with respect to wires of its associated linear polarizer. The two linear polarizers can be rotated 90° with respect to each other or the two quarter-wave plates can be rotated 90° with respect to each other in order for the circular-polarizers 23 to be oppositely-polarized with respect to each other.

As shown in FIGS. 1 and 2, light beam 4a from one of the light emitters 13a can have one polarization (e.g. p or clockwise polarization). A light beam 4b from the other light emitter 13b can have an opposite polarization (e.g. s or counterclockwise polarization, respectively). Thus, the two light beams 4a and 4b can be oppositely-polarized. Because the two light beams 4a and 4b are oppositely-polarized, they will not interfere with each other. As long as the light beams 4a and 4b remain oppositely-polarized, there will be no interference pattern received by the CCD 15.

Fluid 17 can pass through the fluid-flow region 19. A device or means 18 for flowing fluid through the fluid flow region can cause the fluid 17 to flow. The device or means 18 can be a compressed gas source, a differential pressure source, a fan, a pump, or a compressor, or other device that causes the fluid 17 to flow. The fluid 17 can contain particles 14 which can be analyzed by the particle analysis system 10 or 20.

A particle 14 passing through the fluid-flow region 19 and through the two polarized light beams 4a and 4b can affect or change the polarization state of each of the light beams. As the light beams 4a and 4b diffract around the particle, or otherwise are affected by the particle 14, their polarization states can change. After this change in polarization state of the light beams 5a and 5b, the light beams 5a and 5b can interfere with each other, thus creating an interference pattern 6. This interference pattern 6 can be received by the CCD 15.

Particle 14 quantity can be determined by recording each receipt of an interference pattern 6 by the CCD. If the frequency of particles 14 passing the CCD is not too high, then each interference pattern can correlate to a single particle 14 passing the CCD.

An analyzer 16 can be electrically coupled to the CCD 15. The analyzer 16 can analyze input from the CCD 15 to determine particle 14 size and/or shape. The analyzer 16 can compare the interference pattern 6 from the CCD 15 to a library of the interference patterns in order to determine particle 14 size and/or shape. The library can be developed initially by receiving interference patterns of particles of a known size and shape.

Initial particle analysis for the library, and confirmation of particle size and shape, may be improved by use of different types of polarizers. For example, the library may contain first interference patterns, of known particle sizes and shapes, formed by emission of two light beams 4a and 4b of oppositely-polarized, linearly-polarized light. Additionally, the library may contain second interference patterns, of known particle sizes and shapes, formed by emission of two light beams 4a and 4b of oppositely-polarized, circularly-polarized light. Determination of an unknown particle's size and shape may be determined by use of emission of linearly-polarized light and comparing the resulting interference pattern to the first interference patterns in the library, then also by emission of circularly polarized light and comparing the resulting interference pattern to the second interference patterns in the library.

For proper operation of the particle analysis systems 10 and 20, it can be important for the light beams 4a and 4b, emitted from the light emitters 13a and 13b respectively, to be coherent. This can be accomplished by use of dual lasers emitting coherent, polarized light beams 4a and 4b into the fluid-flow region 19. The lasers can be rotated 90° with respect to each other in order for the polarized light beams 4a and 4b to be oppositely-polarized with respect to each other.

Emission of coherent light beams 4a and 4b into the fluid-flow region 19 can also be accomplished if the light source 11 emits coherent light (i.e. is a coherent light source), or by proper size of the polarization devices 23 and proper spacing between the polarization devices 23. Thus, each polarization devices 23 can be disposed at a different opening in the screen 12, and each opening can be sized and shaped to change incident incoherent light from the light source 11 into coherent light 4 on an opposite side of the screen 12 from the light source 11. The polarization devices 23 can be spaced apart by a distance D (FIG. 3) from each other and a portion of the screen $12_p$ (FIG. 3) can be disposed between the polarization devices 23. The proper spacing can depend on the wavelength of incoming light 3 from the light source 11. In one embodiment, the polarization devices 23 can be spaced apart from each other by a distance D of between 0.1 millimeters and 10 millimeters.

Stray light (i.e. light entering the fluid flow region from a source other than the light emitters 13) impinging on the CCD can interfere with the desired interference pattern 6. Thus, it can be important to block stray light. In one embodiment, the screen 12 can be opaque to light (except for the openings where the light emitters 13 are disposed). Also, the fluid-flow region 19 can include a boundary that is opaque to light and that blocks light from entering the fluid-flow region 19 except from the light emitters 13.

A method of determining particle 14 size, shape, quantity, or combinations thereof, can include some or all of the following steps. The method can be done in the following order. Some of the steps can be done simultaneously.

1. Blocking light from entering a fluid flow region 19 (except through or from two light emitters 13, which can be disposed in a light blocking screen 12).
2. Emitting two polarized light beams 4a and 4b, that are oppositely polarized with respect to each other, into the fluid flow region 19.
   a. Each of the two polarized light beams 4a and 4b can be a coherent light beam.
   b. The light beams 4a and 4b can be emitted from two polarization devices 23a and 23b. The polarization devices 23 can be oppositely-polarized with respect to each other. The two polarization devices 23a and 23b can be spaced apart from each other.
   c. The light beams 4a and 4b can be emitted from each of the two lasers. The lasers can be rotated with respect to each other in order to emit the oppositely polarized light beams 4a and 4b.
   d. The light emitters 13 can be disposed in a light blocking screen 12.
3. Passing a particle 14 in or through the fluid flow region 19 past the two light beams 4a and 4b. Polarization states of the light beams 4a and 4b can change due to interaction with the particle 14. Due to the changed polarization states of the light beams 5a and 5b after passing the particle 14, the light beams 5a and 5b can interfere with each other to form an interference pattern 6.
4. Exposing a charge couple device camera (CCD) 15 to the interference pattern 6.
5. Analyzing the interference pattern 6 to determine particle 14 size, shape, quantity, or combinations thereof.
6. Comparing the interference pattern 6 to a library of interference patterns to determine particle 14 size, shape, quantity, or combinations thereof.
7. Step 3 can further comprise:
   a. Flowing a fluid 17 through the fluid-flow region 19. The fluid 17 can include multiple particles 14. Each of the multiple particles 14 can change the polarization state of the light beams 4a and 4b.
   b. Forming multiple interference patterns 6 by the light beams 5a and 5b interference with each other after passing each of the multiple particles 14; and
   c. Exposing the CCD 15 to the multiple interference patterns 6.
   d. Analyzing the multiple interference patterns 6 to determine particle 14 size, shape, quantity, or combinations thereof.

What is claimed is:

1. A particle analysis system comprising:
   a. an unpolarized light source directed towards a charge couple device camera (CCD);
   b. a fluid-flow region disposed between the light source and the CCD;
   c. a light-blocking screen disposed between the light source and the fluid-flow region; and
   d. two polarization devices, oppositely-polarized with respect to each other, disposed in the screen, and capable of allowing light from the light source to pass through the polarization devices, through the fluid-flow region, and onto the CCD.

2. The system of claim 1, further comprising an analyzer electrically coupled to the CCD, the analyzer capable of analyzing input from the CCD for determination of particle size, shape, quantity, or combinations thereof.

3. The system of claim 2, wherein the analyzer is capable of comparing an interference pattern from the CCD to a library of interference patterns in order to determine particle size, shape, quantity, or combinations thereof.

4. The system of claim 1, wherein:
   a. a polarization state of a light beam passing through one of the polarization devices is affected by a particle's shape;
   b. a polarization state of a light beam passing through another of the polarization devices is affected by the particle's shape;
   c. the light beams interfere after polarization states of the light beams are affected by the particle, forming an interference pattern; and
   d. the CCD receives the interference pattern.

5. The system of claim 4, further comprising an analyzer electrically coupled to the CCD, the analyzer capable of analyzing the interference pattern for determination of particle size, shape, quantity, or combinations thereof.

6. The system of claim 1, wherein the screen is opaque to light except through the polarization devices.

7. The system of claim 1, further comprising a boundary of the fluid-flow region that is opaque to light and that blocks light from entering the fluid-flow region except through the polarization devices.

8. The system of claim 1, wherein the light source is a coherent light source.

9. The system of claim 1, wherein each polarization device is disposed at a different opening in the screen, and each opening is sized and shaped to change incident incoherent light from the light source into coherent light on an opposite side of the screen from the light source.

10. The system of claim 1, further comprising a means for flowing fluid through the fluid-flow region.

11. The system of claim 1, wherein the two polarization devices are spaced apart from each other and a portion of the screen is disposed between the polarization devices.

12. The system of claim 1, wherein the two polarization devices are spaced apart from each other by a distance of between 0.1 millimeters and 10 millimeters.

13. A particle analysis system comprising:
   a. two polarized light emitters, oppositely-polarized with respect to each other, disposed at a perimeter of a fluid-flow region, and capable of emitting two beams of oppositely polarized light through the fluid-flow region and onto a charge couple device camera (CCD);
   b. an analyzer electrically coupled to the CCD, the analyzer capable of analyzing input from the CCD for determination of particle size, shape, quantity, or combinations thereof.

14. The system of claim 13, further comprising:
   a. an unpolarized light source directed towards the CCD;
   b. an opaque, light-blocking screen disposed between the light source and the fluid-flow region; and
   c. the two polarized light emitters are two polarization devices and the two polarization devices are:
      i. spaced apart from each other;
      ii. oppositely-polarized with respect to each other;
      iii. disposed in the screen; and
      iv. capable of allowing light from the light source to pass through the polarization devices, through the fluid-flow region, and onto the CCD.

15. A method of determining particle size, shape, quantity, or combinations thereof, the method comprising the following steps in order:

a. emitting two polarized light beams, that are oppositely polarized with respect to each other, into a fluid flow region;
b. passing a particle in the fluid flow region past the two light beams, the particle changing the polarization states of the light beams so that the light beams interfere with each other after passing the particle to form an interference pattern; and
c. exposing a charge couple device camera (CCD) to the interference pattern.

16. The method of claim 15, further comprising analyzing the interference pattern to determine particle size, shape, quantity, or combinations thereof.

17. The method of claim 15, further comprising comparing the interference pattern to a library of interference patterns to determine particle size, shape, quantity, or combinations thereof.

18. The method of claim 15, wherein each of the two polarized light beams is a coherent light beam.

19. The method of claim 15, wherein passing a particle in a fluid flow region further comprises:
a. flowing a fluid through the fluid-flow region, the fluid including multiple particles, each of the multiple particles changing the polarization state of the light beams; and
b. forming multiple interference patterns by the light beams interference with each other after passing each of the multiple particles; and
c. exposing the CCD to the multiple interference patterns.

20. The method of claim 19, further comprising analyzing the multiple interference patterns to determine particle size, shape, quantity, or combinations thereof.

21. The method of claim 15, further comprising two polarization devices disposed in a light blocking screen, the polarization devices being oppositely-polarized with respect to each other, and wherein one of the two polarized light beams is emitted from one of the polarization devices and another of the two polarized light beams is emitted from another of the polarization devices.

22. The method of claim 21, further comprising blocking light from entering the fluid flow region except through the two polarization devices.

23. The method of claim 21, wherein the two polarization devices are spaced apart from each other.

24. The method of claim 21, wherein the two polarization devices are linear polarizers.

25. The method of claim 21, wherein the two polarization devices are circular-polarizers.

* * * * *